United States Patent
Wellisz et al.

(10) Patent No.: US 7,048,737 B2
(45) Date of Patent: *May 23, 2006

(54) CRANIAL BONE FLAP FIXATION SYSTEM AND METHOD

(75) Inventors: Tadeusz Z. Wellisz, Los Angeles, CA (US); Cin K. Abidin, Los Angeles, CA (US); Dean Gray, Los Angeles, CA (US)

(73) Assignee: Bioplate, Inc., Los Angeles, CA (US)

( * ) Notice: Subject to any disclaimer, the term of this patent is extended or adjusted under 35 U.S.C. 154(b) by 659 days.

This patent is subject to a terminal disclaimer.

(21) Appl. No.: 10/171,555

(22) Filed: Jun. 11, 2002

(65) Prior Publication Data

US 2003/0229349 A1    Dec. 11, 2003

(51) Int. Cl.
*A61B 17/58* (2006.01)
(52) U.S. Cl. .......................................... 606/70; 606/99
(58) Field of Classification Search ............ 606/69–73, 606/76, 213, 104, 215, 216, 232; 623/17, 623/17.19; 29/243.523, 243, 523; 72/243.528
See application file for complete search history.

(56) References Cited

U.S. PATENT DOCUMENTS

| | | | |
|---|---|---|---|
| 3,540,106 A * | 11/1970 | Goldman ..................... 29/268 |
| 4,050,464 A * | 9/1977 | Hall ............................ 606/61 |
| 5,250,049 A | 10/1993 | Michael | |
| 5,342,393 A | 8/1994 | Stack | |
| 5,549,620 A | 8/1996 | Bremer | |
| 5,666,710 A * | 9/1997 | Weber et al. .......... 29/243.523 |
| 5,707,373 A | 1/1998 | Sevrain et al. | |
| 5,800,436 A * | 9/1998 | Lerch .......................... 606/72 |
| 6,258,091 B1 | 7/2001 | Sevrain et al. | |
| 6,270,500 B1 * | 8/2001 | Lerch .......................... 606/72 |
| 6,379,363 B1 * | 4/2002 | Herrington et al. ........... 606/79 |
| 6,641,588 B1 * | 11/2003 | Citron et al. ................ 606/103 |
| 2002/0016593 A1 | 2/2002 | Hearn et al. | |
| 2002/0169455 A1 * | 11/2002 | Bannerman et al. .......... 606/99 |

FOREIGN PATENT DOCUMENTS

| | | |
|---|---|---|
| JP | 50-110090 | 8/1975 |
| JP | 5-220174 | 8/1993 |
| SU | 1600713 A1 | 10/1990 |
| WO | WO 00/49949 | 8/2000 |
| WO | WO 02/09602 A1 | 2/2002 |

* cited by examiner

*Primary Examiner*—Anhtuan T. Nguyen
(74) *Attorney, Agent, or Firm*—William W. Haefliger

(57) ABSTRACT

A cranial bone and bone flap fixation device, comprising first and second caps between which portions of the cranial bone and bone flap are to be gripped; a mounting post located to allow relative cap movement lengthwise of an axis defined by the post, at least the first cap, which is movable lengthwise of the post, forming peripheral petals that are spaced apart about an axis and radially outwardly of a central body portion of the cap, whereby the petals are individually and resiliently movable relative to the central body portion in directions generally parallel to the axis, and in response to gripping.

17 Claims, 20 Drawing Sheets

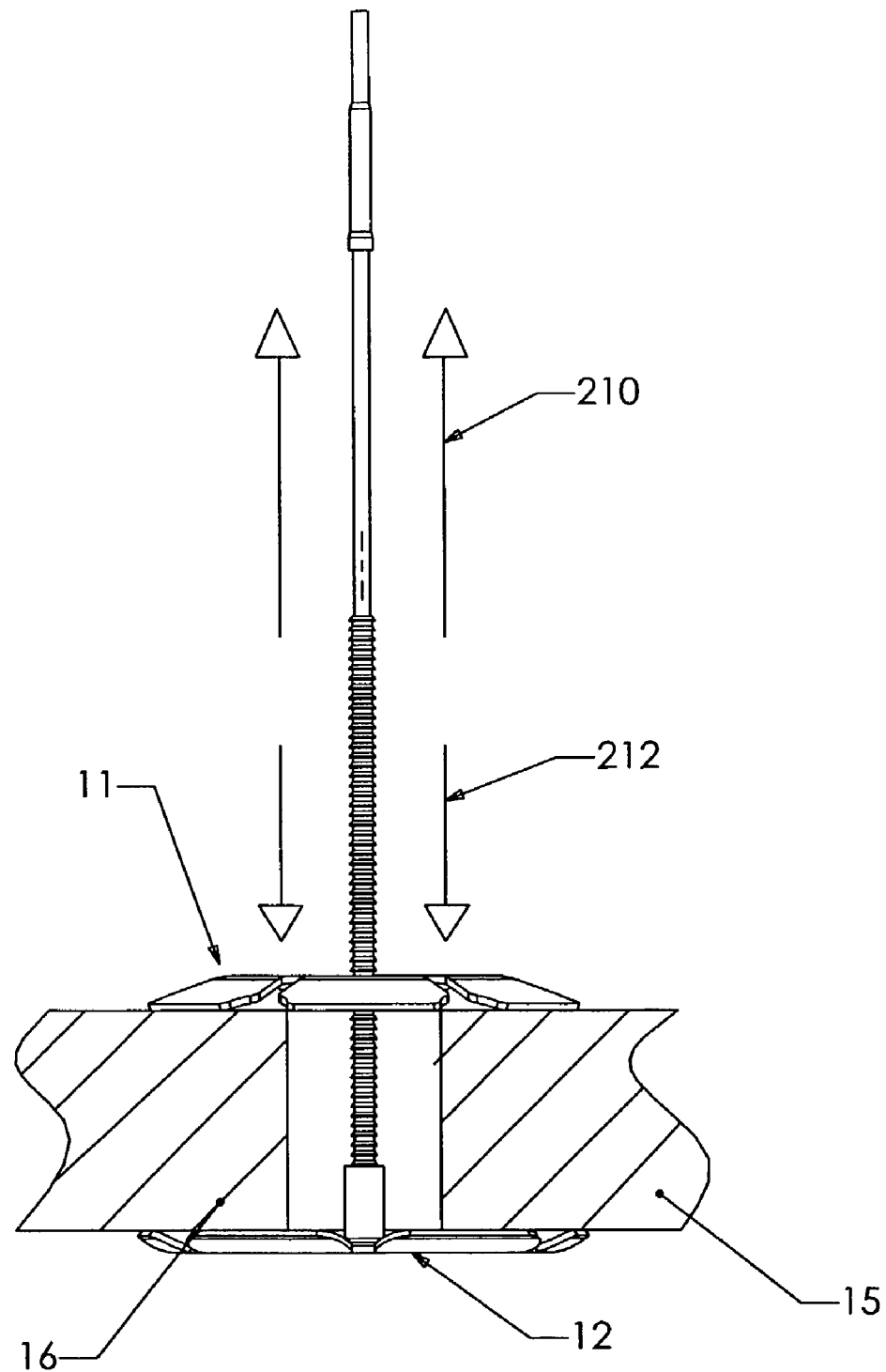

CRANIAL BONE FLAP FIXATION SYSTEM AND METHOD

BACKGROUND OF THE INVENTION

This invention relates generally to cranial surgery apparatus and method, and more particularly to implant systems and methods for re-fixation of cranial bone flaps after craniotomy.

Cranial bone flaps after craniotomy are typically fixed in position with wire, suture material or mini plates and screws. In some cases, fixation with wire or suture material is not secure. Shifting of the bone flap may result in dislocation, causing depression or protrusion of the flap relative to the adjacent cranium. This phenomenon occurs more frequently with the progressive shift to smaller craniotomies for minimally invasive surgical procedures.

Fixation of the bone flap using mini plates and screws has improved the attachment of the bone flap. This technique, however, demands a considerable amount of time and added cost. There is need for an improved system for fixation of the bone flap to the cranium, providing for quick and easy application, optimal stability, and reliable fixation of the bone flap to the cranium.

SUMMARY OF THE INVENTION

It is a major object of the invention to provide improved flap fixation apparatus, system and methods meeting the above needs. Basically, the fixation device of the invention comprises:

a) first and second caps between which portions of the cranial bone and bone flap are to be gripped, b) a mounting post located to allow relative cap movement lengthwise of an axis defined by the post, c) at least the first cap forming peripheral petals that are spaced apart about said axis and radially outwardly of a central body portion of the cap, whereby the petals are individually and resiliently movable relative to said central body portion in directions generally parallel to the axis, and in response to such gripping.

Another object includes provision of fixation petals at one or both caps, and having widths which decrease in directions toward the axis, to define flexure zones spaced between said axis and portions of the petals furthest from said axis, whereby cap and petal conformation to gripped flap and cranial elements is enhanced. Typically, such petals may have flexible zones spaced between the axis and portions of the petals furthest from said axis. Further, one cap is typically attached to an end of the post, and the other cap is adjustably movable along the post toward the one cap, the petals of each cap having bone engaging peripheral portions angled toward the space between the caps.

Another object is to provide a post having axially spaced retention shoulders, the other cap having circularly spaced tabs projecting generally toward said axis, and which have ratcheting engagement with such shoulders as the other cap is moved toward the one cap, the shoulders typically blocking retraction of said other cap. Such tabs are typically spaced about the post axis, and are individually resiliently flexible in directions generally parallel to said axis.

A further object is to provide improved tabs having widths less than their lengths, and that define tips that have said ratcheting engagement with post shoulders. The number of such tabs is typically less than the number of petals; and the number of petals is such as to enable between two and four petals to engage the bone flap, and two to four petals to engage the cranial bone.

Yet another object includes a method of use of the device, which includes:

a) relatively displacing the caps toward one another to engage the petals of one cap with at least the bone flap or the adjacent cranial zone, and to conformingly retain the caps including said petals to opposite sides of the bone flap and the cranial bone, b) and tightening the caps toward one another into a positions wherein relative separation of the caps is blocked, petals are resiliently flexed, and post extent between the caps is tensioned.

An additional object is to provide for cap self centering functionality, as by provision of a cap guide configured to extend into a gap formed between the cranial bone and bone flap, to laterally orient the one cap so that petal portions thereof will overlap the cranial bone and bone flap to approximately equal lateral extents. That guide may have an axially tapering surface or surfaces to project into the gap between edges of said cranial bone and bone flap; and the guide may comprise a cup-shape or tapering tabs, as will be seen. Both caps may incorporate such self-centering functionality.

A further object comprises provision of a cover extending over a cavity formed by the protruding guide, and attached to said one cap.

These and other objects and advantages of the invention, as well as the details of an illustrative embodiment, will be more fully understood from the following specification and drawings, in which:

DRAWING DESCRIPTION

FIG. 16 is a top plan view of a modified top or upper cap, for use with the FIG. 14 cap, and a post as referred to;

FIGS. 28a–28c are schematic showings of cap installation;

DETAILED DESCRIPTION

Figure 1:
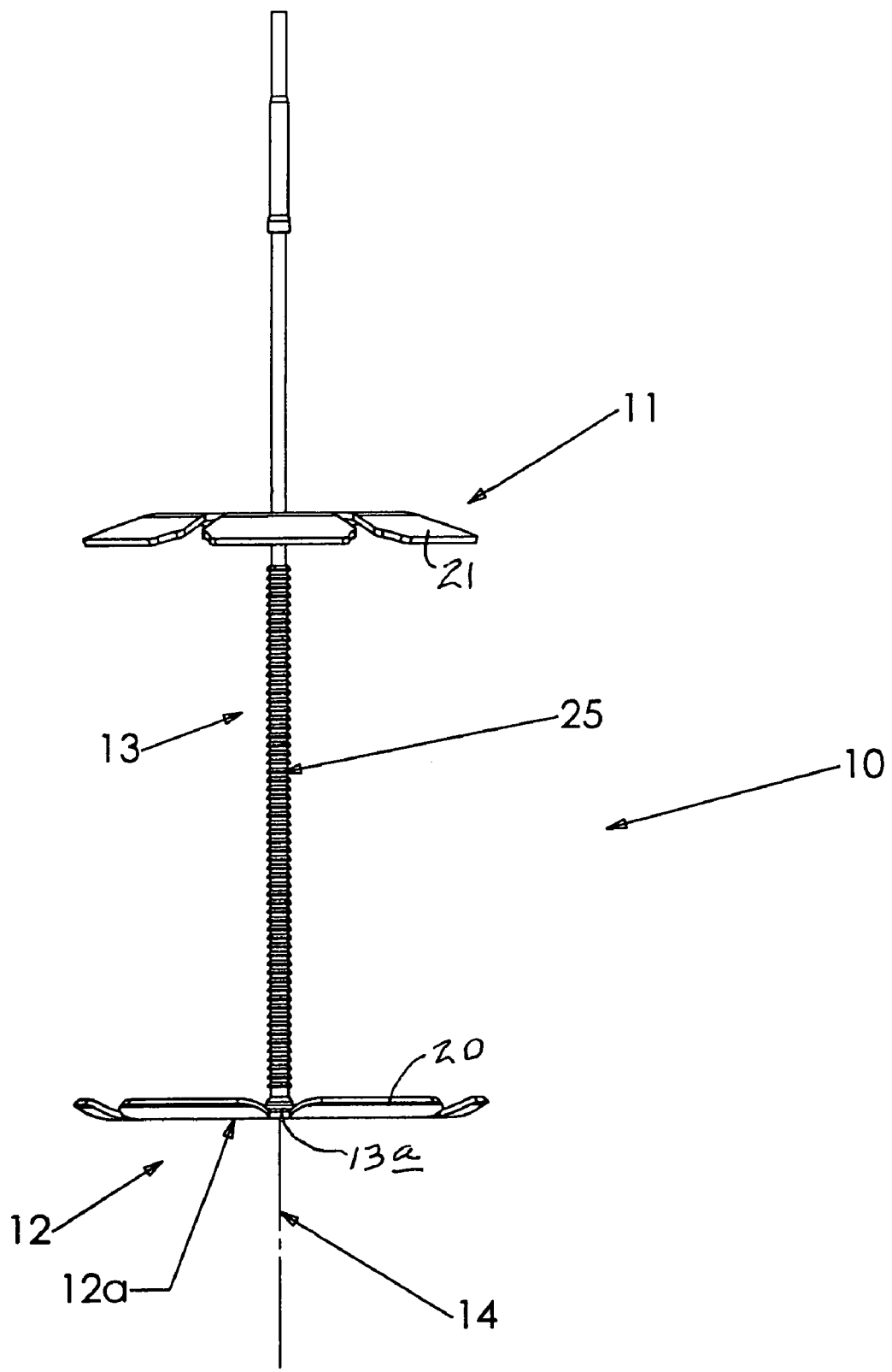
FIG. 1 is a side elevation showing top and bottom caps, and a post.
Figure 2:
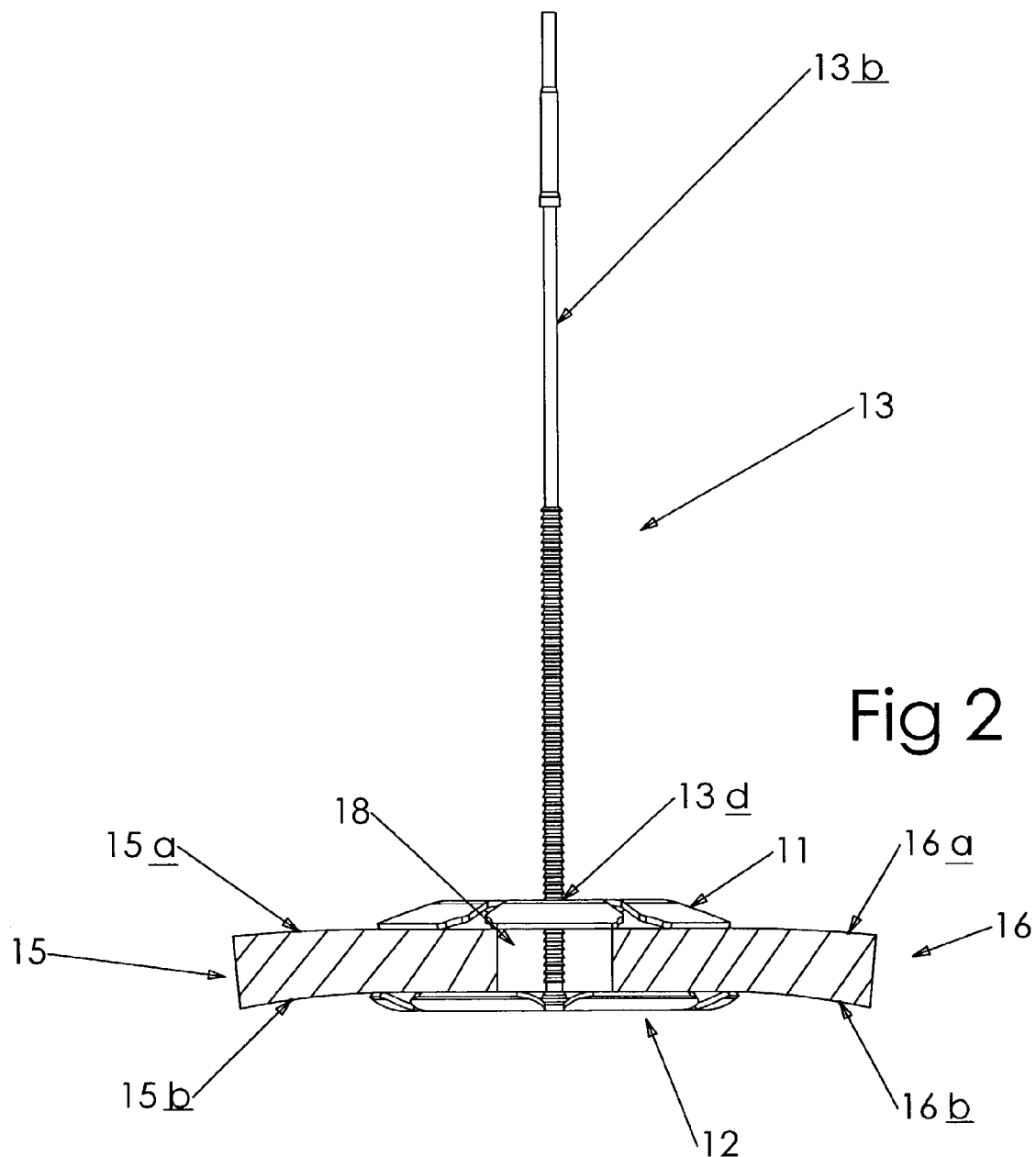
FIG. 2 is like FIG. 1, but the caps have been relatively moved toward a bone flap and cranial bone.

In FIG. 1 the cranial bone and bone flap fixation device 10 comprises first and second caps 11 and 12 between which portions of cranial bone and bone flap are to be gripped. A mounting post 13 is located to allow relative cap movement lengthwise of an axis 14 defined by the post. FIG. 2 shows the caps after such relative movement toward one another, to close toward and against upper and lower, or opposite surfaces 15a and 15b of cranial bone 15, and against upper and lower, or opposite, surfaces 16a and 16b of bone flap 16. Typically, the lower end 13a of post 13 is attached to or integral with the central region 12a of cap 12, and projects through kerf or gap 18 formed between 15 and 16 during surgery, and through cap 11. The caps are urged toward one another while in engagement with surfaces 15a and 15b, 16a and 16b, as by upward pulling of the post upper extent 13b and downward pushing of the cap 11. See also FIG. 28.

Petals 20 and 21 on the caps thereby become resiliently deflected, while individually and locally conforming to the bone surfaces and their curvatures, at the points of petal engagement with such surfaces. The use of such petals allows differential bending deflection of the petals to accommodate to desired conformance to bone surface local geometric variation, at such points of engagement. The post 13 may be serrated as shown at 25 to enable one-way ratcheting relative movement of cap 11 toward cap 12, and also to enable positive locking of cap 11 to the post (i.e. shoulder angularity to block cap 11 retraction) after desired forcible petal edge engagement of both caps with the bone and bone flap 15 and 16, as will be further explained. After such locking, the post is severed at region 13d close to the cap 11. Positive locking of the cap 11 to the post assures positive retention of the caps in engagement with upper and lower sides of the cranial bone and bone flap, and resultant positive positioning of the flap in position relative to cranial bone, during and after replacement of the flap to the skull, promoting healing.

Figure 3:
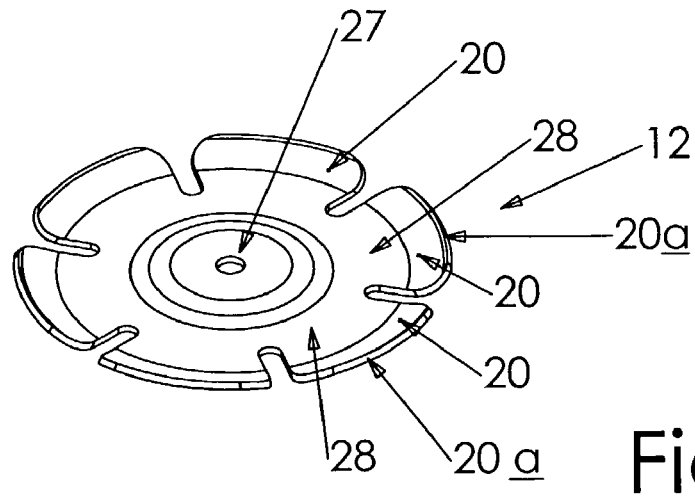
FIG. 3 is a perspective view of the bottom cap seen in FIGS. 1 and 2.
Figure 4:
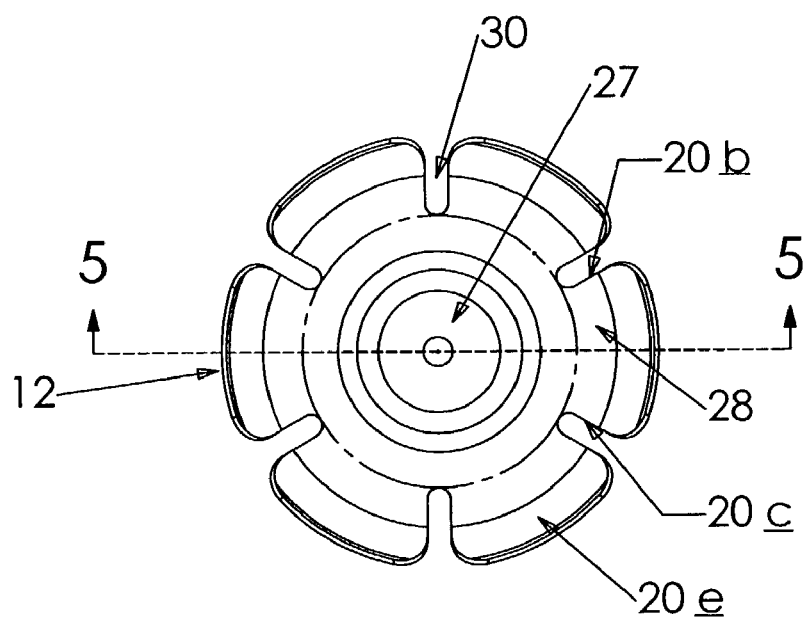
FIG. 4 is an enlarged top plan view of the FIG. 3 cap.
Figure 5:
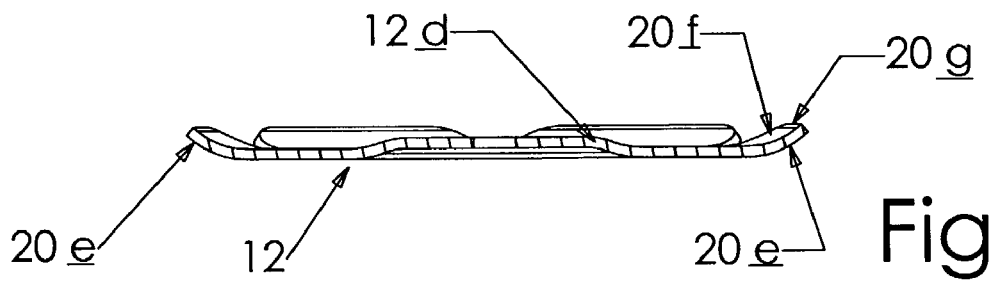
FIG. 5 is a further enlarged section, taken on lines 5—5 of FIG. 4.
Figure 6:
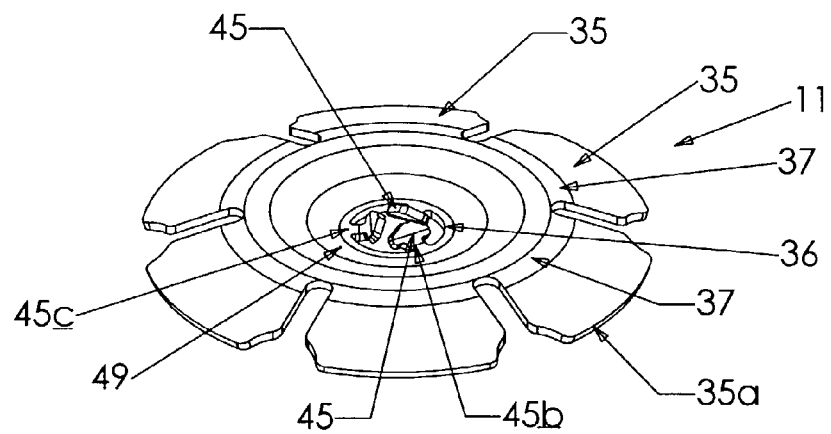
FIG. 6 is a perspective view of the top or upper cap seen in FIGS. 1 and 2.
Figure 10:
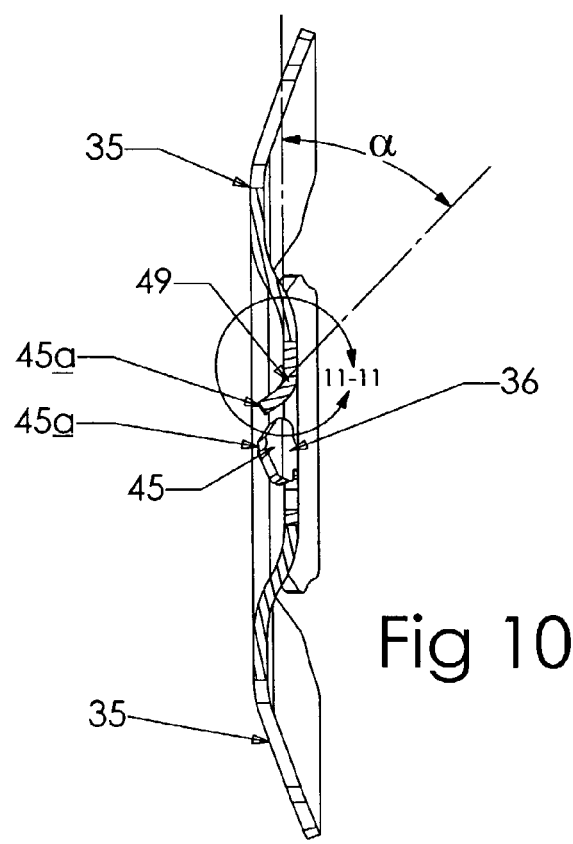
FIG. 10 is an enlarged section taken on lines 11—11 of FIG. 7.
Figure 11:
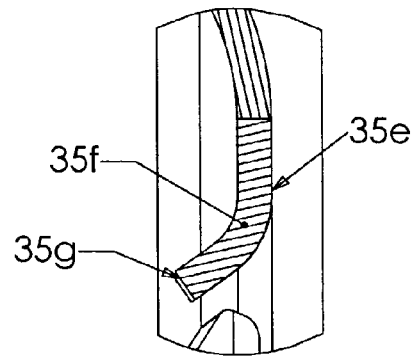
FIG. 11 is a further enlarged fragmentary section taken on lines 11—11 of FIG. 10.
Figure 7:
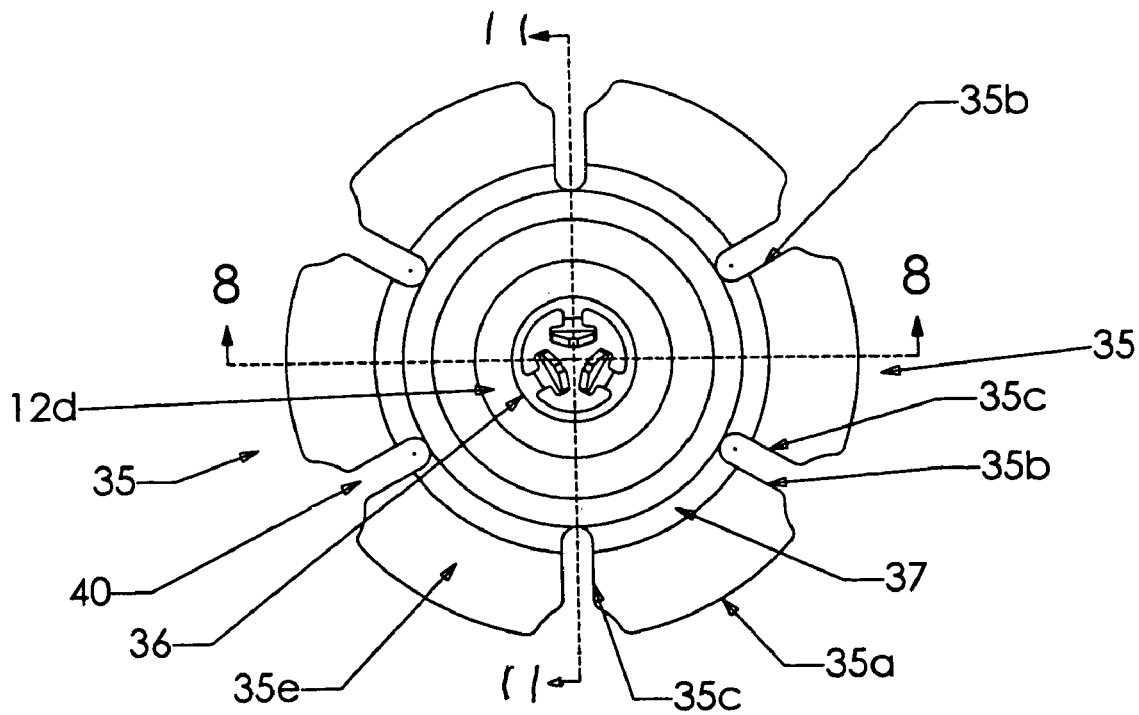
FIG. 7 is a top plan view of the FIG. 6 cap.
Figure 8:
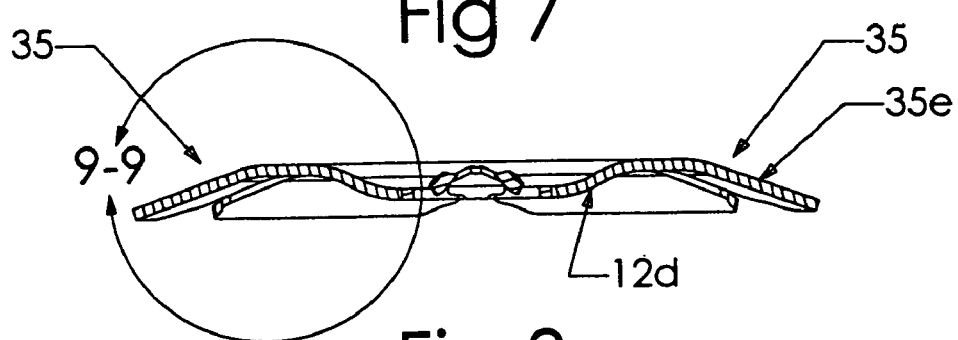
FIG. 8 is an enlarged section taken on lines 8—8 of FIG. 7.
Figure 9:
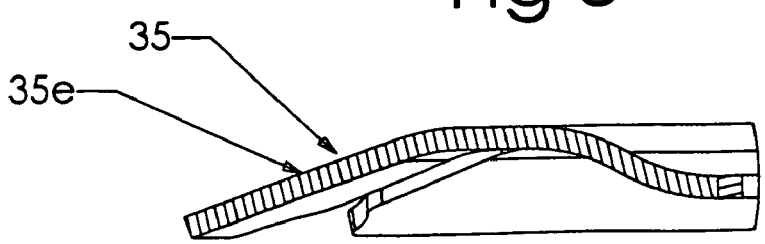
FIG. 9 is a further enlarged fragmentary section taken on lines 9—9 of FIG. 8.

FIGS. 3–5 are views showing one preferred configuration of the petals 20 on lower cap 12. They have widths which decrease in directions toward the cap center region 27, to define narrowed petal flexure zones 28 spaced between center region 27 and peripheral portions 20a of the petals furthest from the center 27, and from post axis 14.

The post is typically attached to the cap 12, at its center. The petals have opposed widthwise spaced edges 20b and 20c, which taper toward center region 27, as shown, increasing petal resilient flexibility at the narrowed width, flexure zones. FIGS. 4 and 5 show that the petals have outermost segments 20e with bi-directional bending, or curvature, as in directions both about axis 14, and also in axial radial planes, for example the plane of FIG. 5, assuring gripping of bone by bent and stiffened petal segment edges. See segment local upward bend at 20f, which also provides an edge 20g for positive gripping of the bone or bone flap material. Between 5 and 7 such segments is preferred, and 6 are shown. Cap controlled stiffness is also enhanced by upward deflection of the cap region 12d inwardly of gaps 30 formed between the petals. The cap preferably consists of titanium (anodized so as not to oxidize) or titanium alloy, or other bio-compatible material. Cap thickness is typically between 0.010 and 0.015 inch.

FIGS. 6–11 are views showing one preferred configuration of petals 35 on upper cap 11. They also have widths which decrease in directions toward cap central region 36, to define flexure zones 37 located between the central region 36 and peripheral portions 35a farthest from region 36, through which post axis 14 extends.

Petals 35 have opposed and widthwise spaced edges 35b and 35c, which relatively taper toward region 36, increasing petal resilient flexibility at the flexure like narrowed width zones. FIGS. 7–10 show that the petals have outermost segments 35e with bi-directional bending or curvature, as in directions both about axis 14, and also in axial radial planes, for example the planes of FIGS. 8–10. Note segment downwardly radiused bend at 35f in FIG. 11, which also provides an edge 35g for positive gripping of the bone or flap material at surfaces 15a and 16a.

Cap controlled stiffness is also enhanced by downward deflection of the cap region 12d inwardly of the gaps 40 formed between the petals. Cap 11 also preferably consists of titanium (anodized) or titanium alloy, or other bio-compatible material, and its thickness is typically between 0.010 and 0.015 inches.

Figure 13:
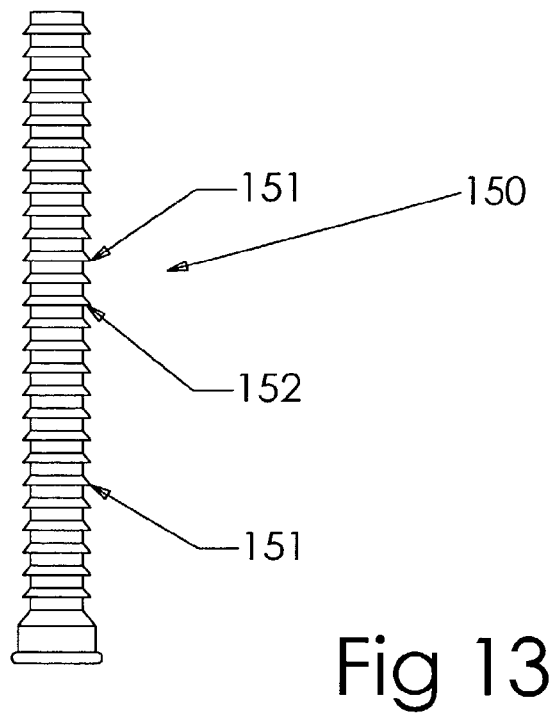
FIG. 13 is an enlarged fragmentary elevation taken on lines 13—13 of FIG. 12.
Figure 12:
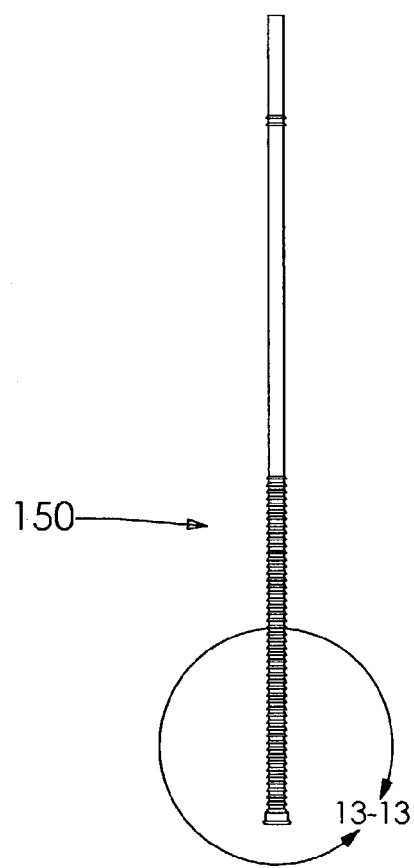
FIG. 12 is a side elevation showing the post as seen in FIG. 2.

Of further importance is the provision of spaced tabs, as at 45, projecting toward and spaced apart about axis 14, so as to have one-way ratcheting engagement of tab narrowed inner edges 45a with the post serrations as the upper cap 11 is displaced along the post relatively toward lower cap 12. The tabs are individually resiliently flexible in directions generally parallel to axis 14, and for that purpose they have narrowed width flexure zones 45b located between edges 45a and the regions 45c of tab jointure with the dished region 49 of the cap. See FIGS. 6, 7, 8 and 10. The tab flexure zones 45b have widths less than the tab length, and the tabs extend at angles α out of the transverse plane of dished region 49, to further such ratcheting engagement with post serrations, and to facilitate locking of the three tab edges 45a into the valley or valleys between successive serrations on the post, to hold the cap petals compressingly against the upper and lower surfaces of the cranial bone and bone flap. The number of tabs is typically less than the number of petals, on the upper cap. Accordingly, an important configuration of the invention comprises:

a) first and second caps between which portions of the cranial bone and bone flap are to be gripped, b) a mounting post located to allow relative cap movement lengthwise of an axis defined by the post, c) one of the caps being attached to an end of the post, the other cap being movable along the post toward said one cap, d) the post having axially spaced retention shoulders, and the other cap has spaced tabs projecting toward said axis, and which have one-way ratcheting engagement with such shoulders as said other cap is moved toward the one cap. FIGS. 12 and 13 show post serrations 150 and one-way ratchet shoulders 151.

Also, the method of affixing a bone flap to an adjacent cranial bone includes the steps:

a) providing first and second caps between which portions of the cranial bone and bone flap are to be gripped, b) providing a mounting post located to allow relative cap movement lengthwise of an axis defined by the post, c) providing at least the first cap with peripheral petals that are spaced apart about said axis and radially outwardly of a central body portion of the cap, whereby the petals are individually and resiliently movable relative to said central body portion in directions generally parallel to said axis, and in response to said gripping, d) relatively displacing the caps toward one another to engage the petals of one cap with at least the bone flap or the adjacent cranial bone, and to conformingly retain the caps including said petals to opposite sides of the flap and the cranial zone, e) tightening the caps relatively toward one another into positions wherein relative separation of the caps is blocked, petals are resiliently flexed, and post extent between the caps is tensioned.

Typically, the lower cap is pulled upwardly, toward the underside of the flap and cranial bone, while the upper cap is lowered, to avoid damage to brain tissue.

Figure 28:
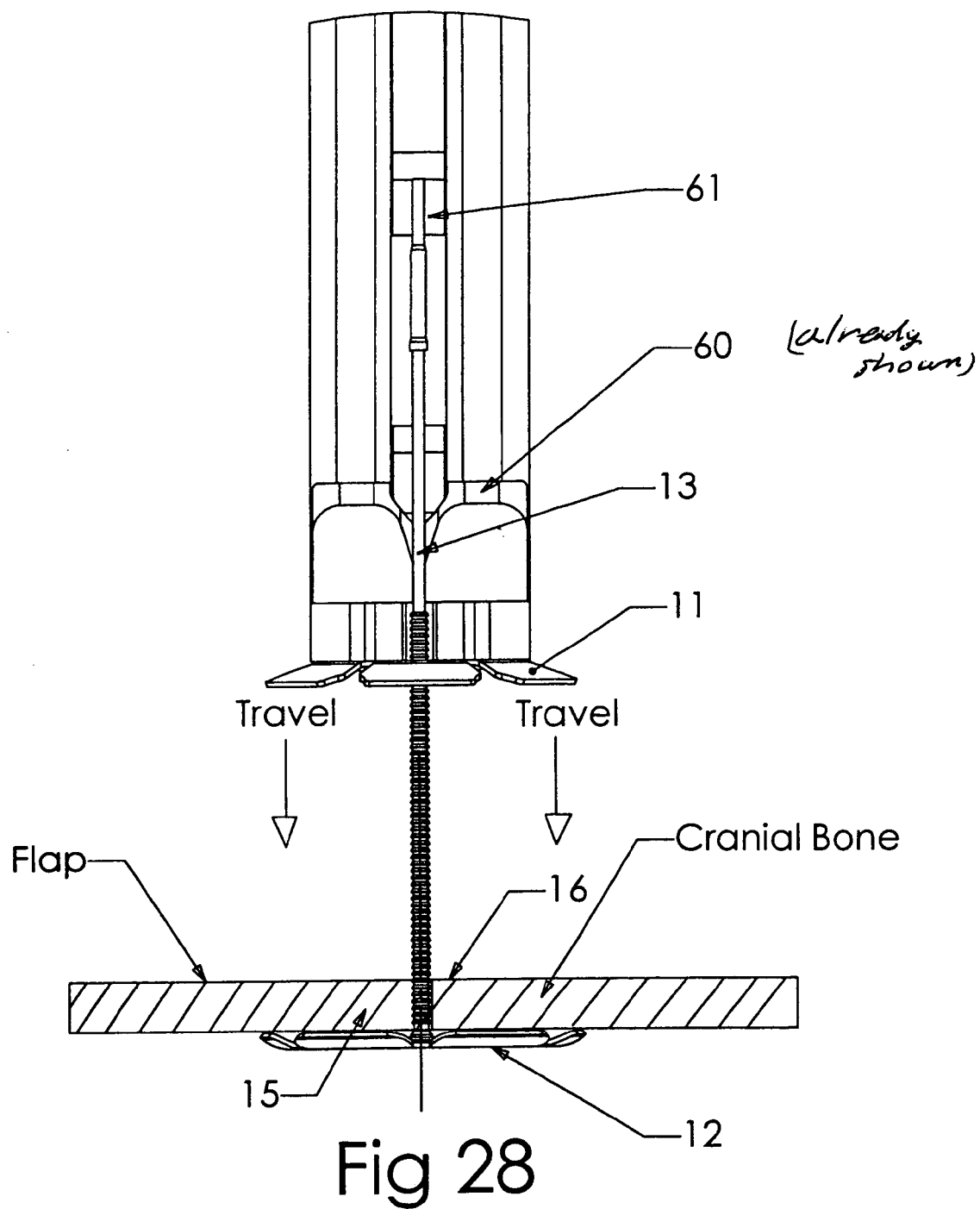
FIG. 28 is a schematic view showing force application, ratcheting action, and relative displacement of the two caps, during use of the device.

FIG. 28 schematically shows a first member 60 or pusher pushing downwardly on the upper cap 11, while a second member 61 holds or positions the post 13, acting to hold the lower cap 12 in position at the undersides of the cranial bone and flap elements 15 and 16. During such downward travel of the upper cap 11 it ratchets along the post serrations, and ultimately becomes tightened against the upper surfaces of 15 and 16, causing petal flexing as referred to. FIGS. 12 and 13 show details of post serrations 151, with barb-like edges 152 tapered forwardly (downwardly).

Figure 28A:
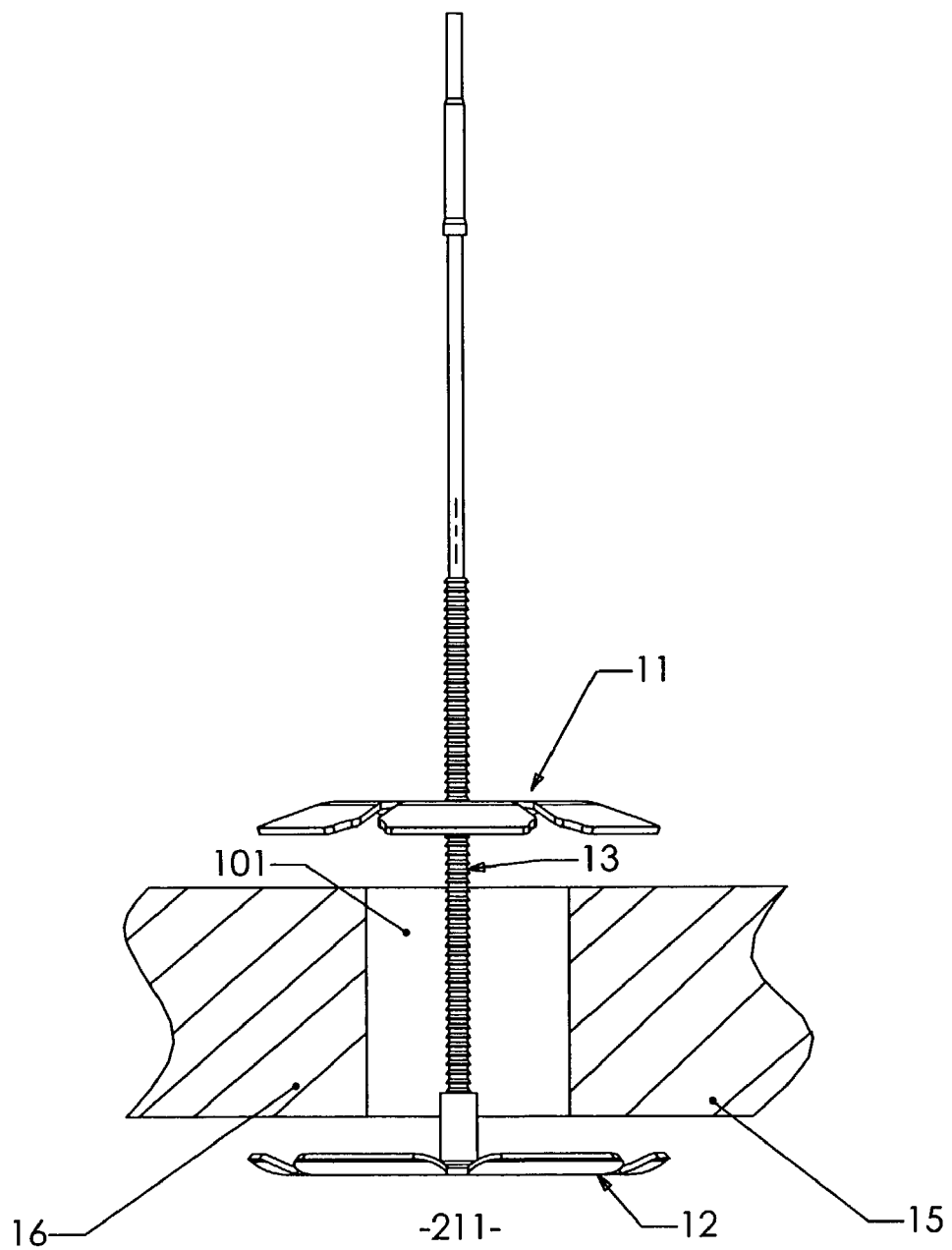
Figure 28B:
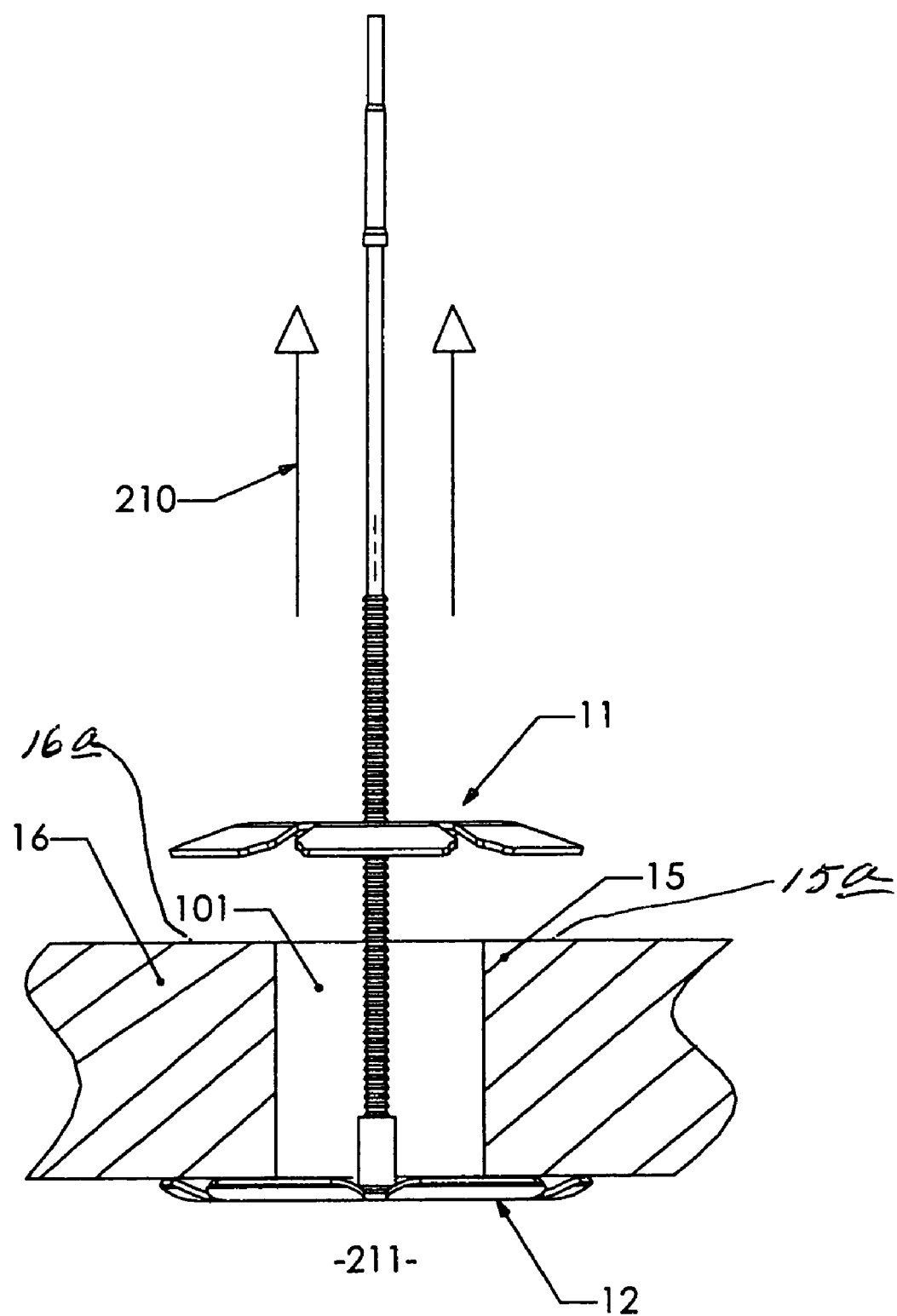
Figure 29:
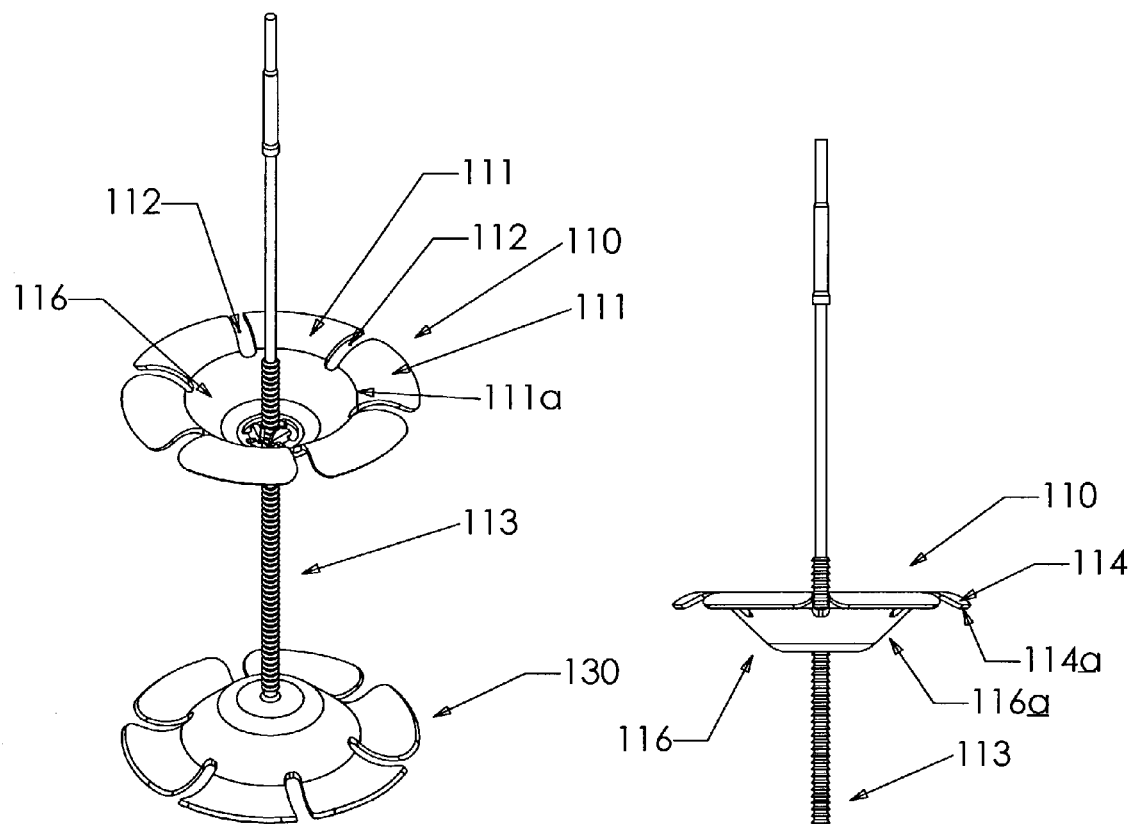
FIG. 29 is a perspective view of a modification.
Figure 30:
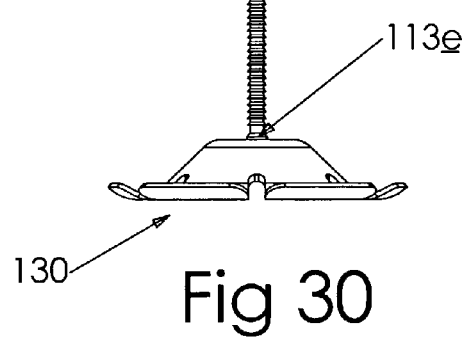
FIG. 30 is an elevational view of the FIG. 29 device.
Figure 31:
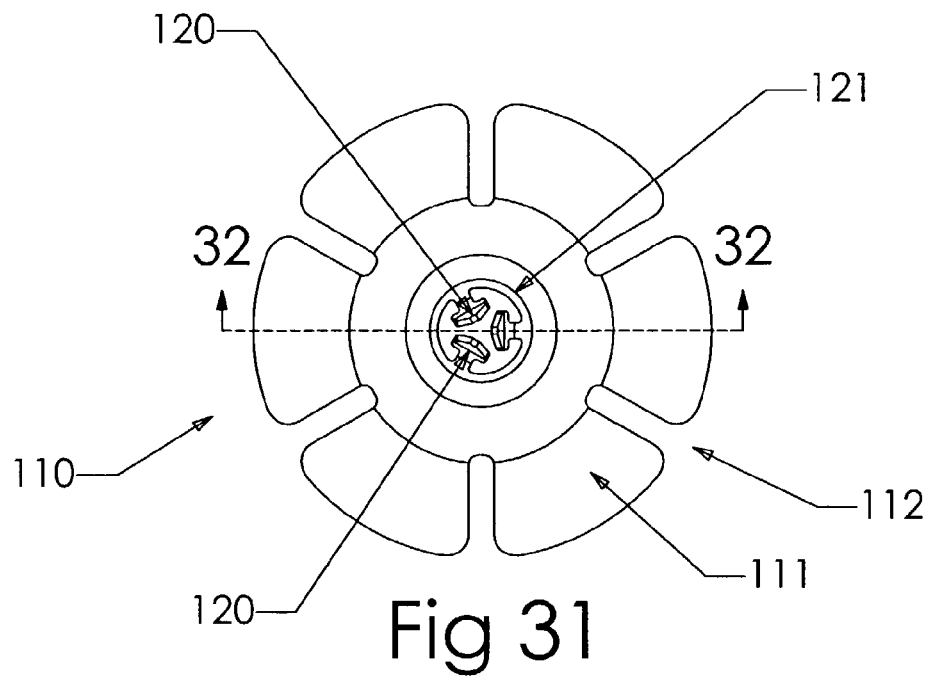
FIG. 31 is a top plan view of the upper cap as also seen in FIGS. 29 and 30.

In the example shown in FIGS. 28*a*–28*c*, initially the stem or post 13 is positioned to extend through the gap 101 between flap and cranial bone elements 15 and 16, with cap 11 at the upper side of the gap, and cap 12 at the lower side of the gap. Next, and as seen in FIG. 28*b*, upward force (for example manual force 210) is exerted on the stem or post 13 to elevate lower cap 12 away from the brain region 211 and against the lower sides of 15 and 16 (to avoid brain damage) as by petal engagement as described. Such upward force exertion is maintained, as the upper cap 11 is then lowered by force exertion 212, to engage the lower cap petals against the upper sides of 15 and 16. The shoulders or teeth on the post are angled to block upward retraction of the lowered tabs 45 and upper cap 11, relative to the post.

Figure 14:
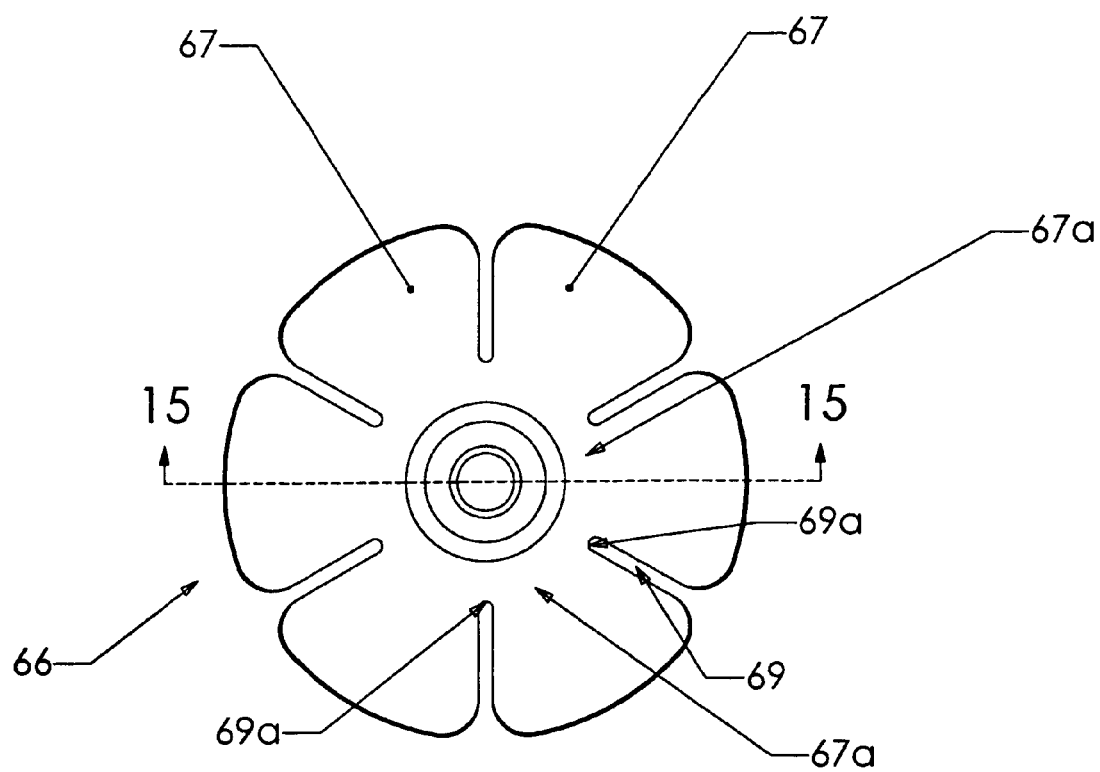
FIG. 14 is a top plan view of a modified bottom cap.
Figure 15:
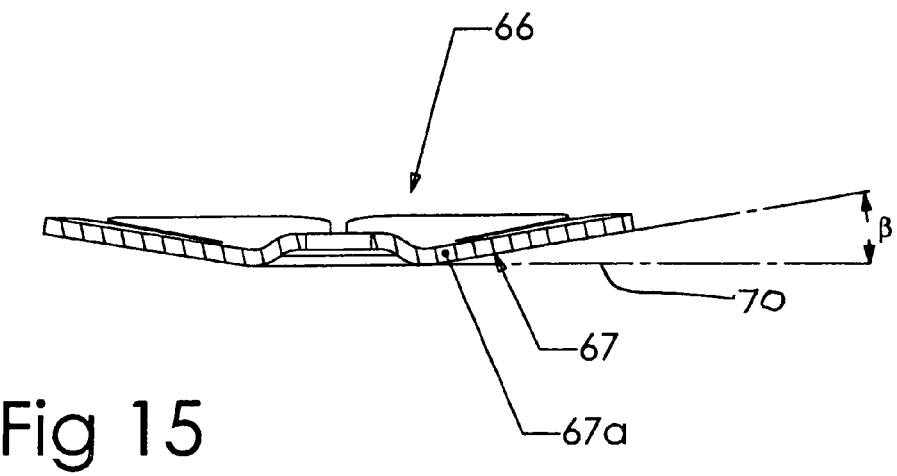
FIG. 15 is a section taken on lines 15—15 of FIG. 14.

FIGS. 14 and 15 show a modified lower cap 66 having six petals 67 spaced apart about a center region 68, with reduced width radial slits 69 between the petals. The latter have narrowed width flexure zones 67*a* between inner terminals 69*a* of the slits. The petals extend at acute angles β, between 15° and 25° relative to a transverse plane 70, throughout the petal radial lengths.

Figure 16:
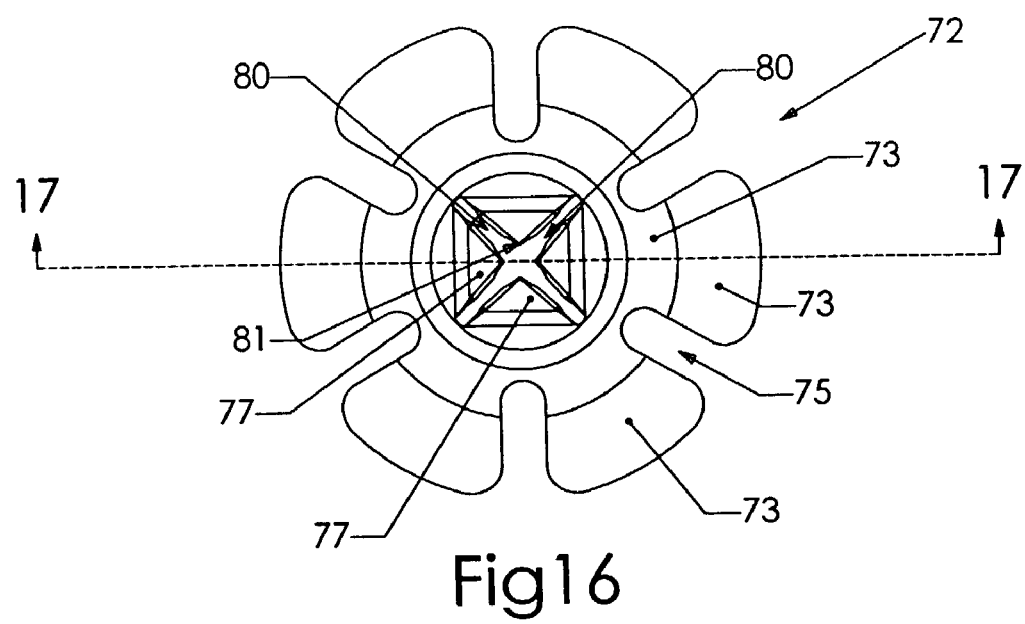
Figure 17:
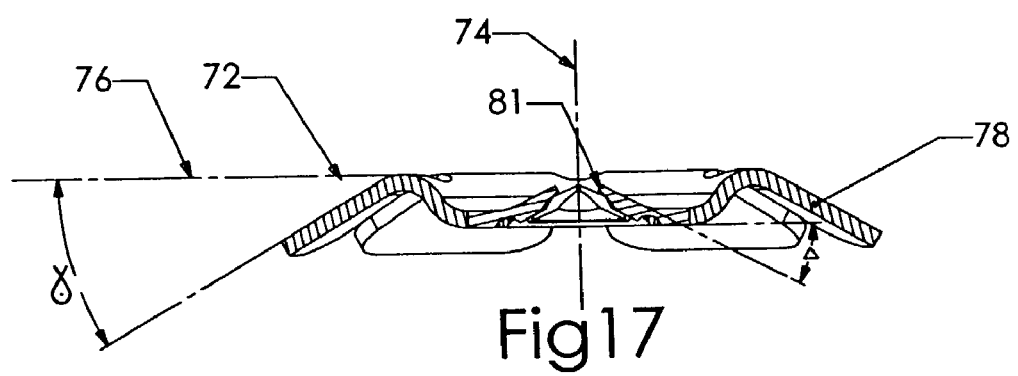
FIG. 17 is a section taken on lines 17—17 of FIG. 16.

FIGS. 16 and 17 illustrate a top or upper cap 72 to be used with cap 66. Cap 72 has six petals 73 spaced apart about an axis 74 corresponding to a serrated post axis, such as axis 14 described above. Note radial slits 75 separating the petals 73 and the petal flexure zones 73*a* of reduced width between inner extents of the slits. The petals extend at angles γ (about 30°) outwardly and downwardly relative to a transverse plane 76, normal to axis 74, throughout or substantially throughout petal radial lengths. Four ratcheting or locating tabs 77 are provided to extend angularly upwardly and inwardly at angles Δ (about 28°) toward axis 74 as seen in FIGS. 16 and 17. The tabs are spaced apart by four gaps 80, and they taper toward inner tips 81 that engage and ratchet on and over the post serrations, such ratcheting characterized by resilient deflection of the tabs as tips 81 ride over the outer edges of the post serrations. Also, the tips lock into the serration valley corresponding to tightened positioning of the upper and lower caps.

Figure 18:
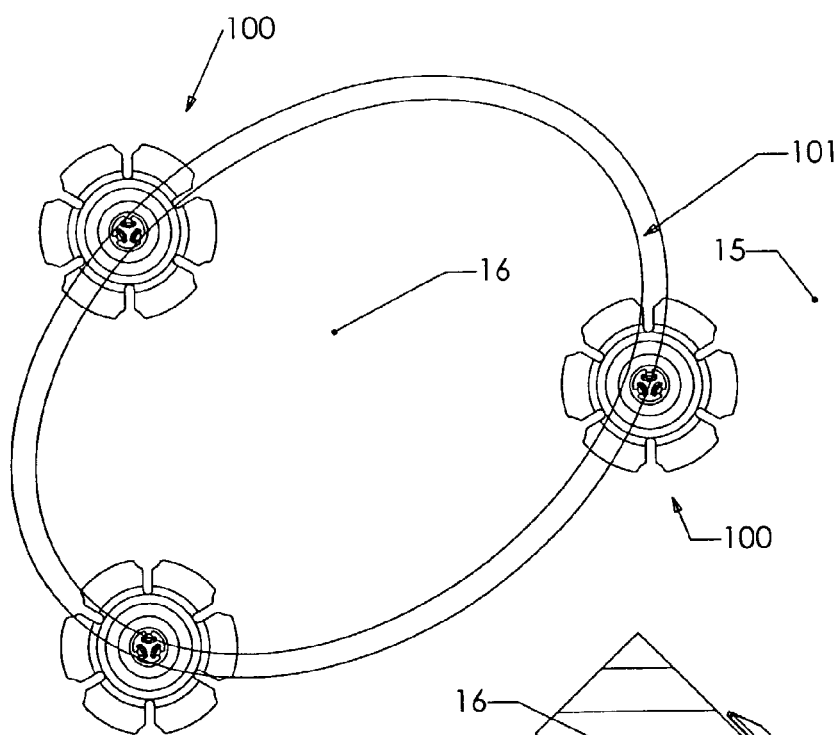
FIG. 18 is a perspective view of a system of upper and lower caps, applied to a bone flap and to cranial bone, and bridging the gap therebetween.
Figure 19:
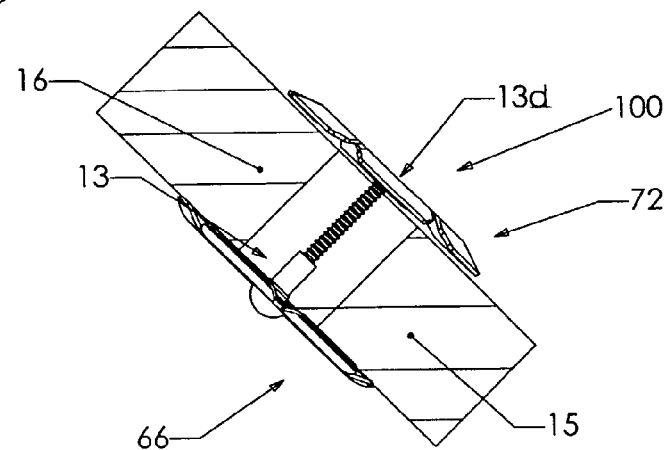
FIG. 19 is an enlarged section showing upper and lower caps and a post, fixing a bone flap in position relative to cranial bone.

FIG. 18 shows emplacement of multiple like devices 100 of the type seen in FIGS. 14–17, to extend across a gap or kerf 101 formed between cranial bone and bone flap elements 15 and 16. Variable surface curvature of those bone elements, at the location of devices 100 is accommodated by variable petal flexing, as described above. See also FIG. 19.

Figure 20:
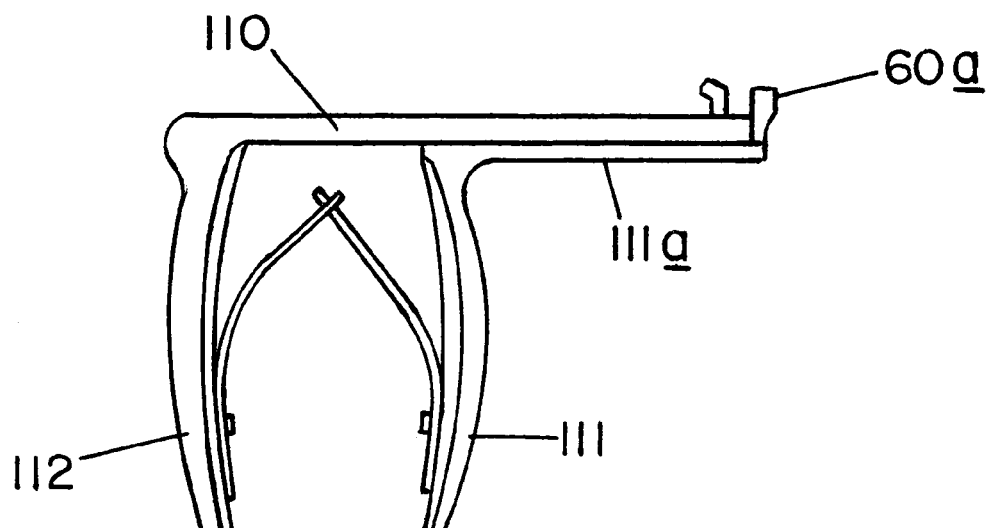
FIG. 20 is a side elevation showing an applicator.
Figure 21:
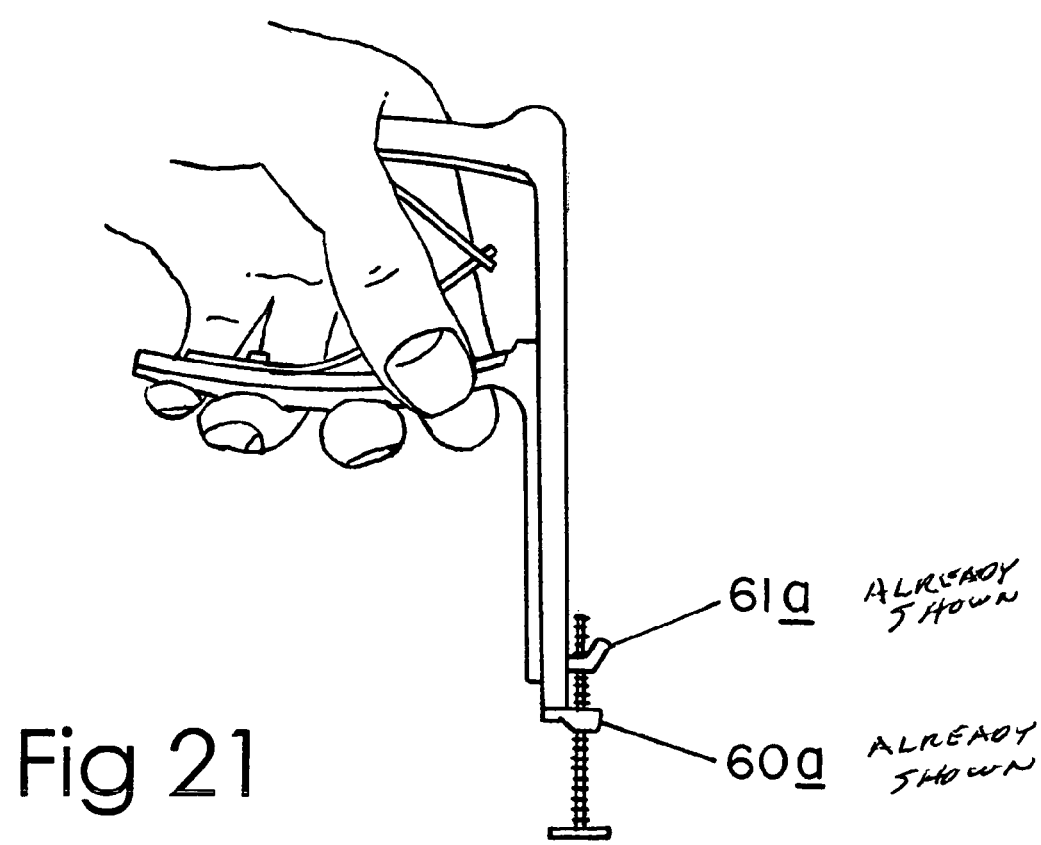
FIG. 21 is a view like FIG. 20 showing the applicator holding a post and upper and lower supported caps.
Figure 27:
FIG. 27 is an enlarged fragmentary section taken on lines 27—27 of FIG. 25.
Figure 22:
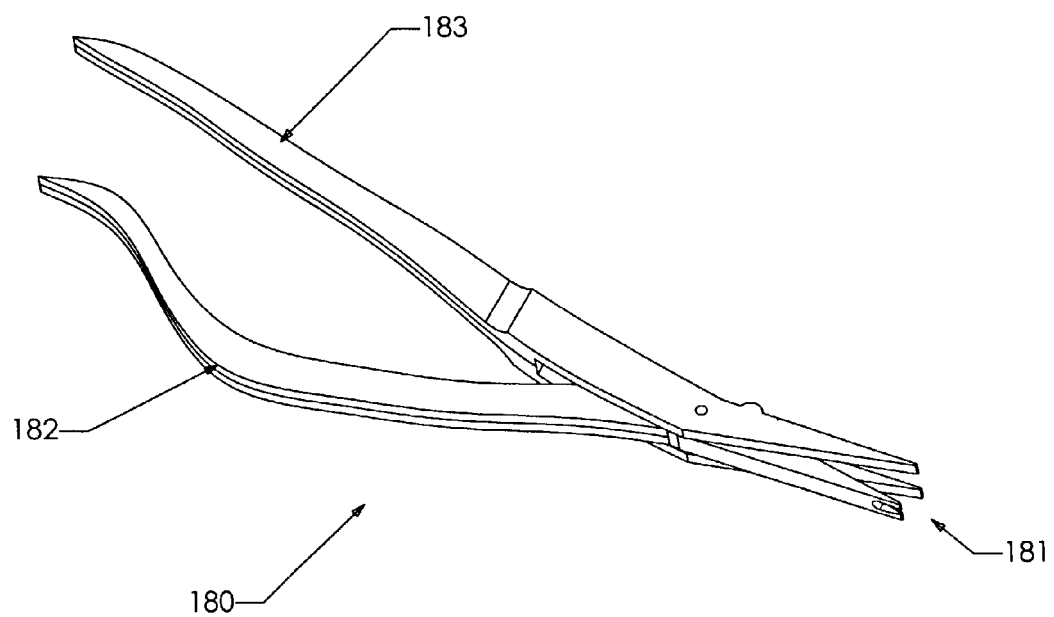
FIG. 22 is a perspective view showing another applicator.
Figure 24:
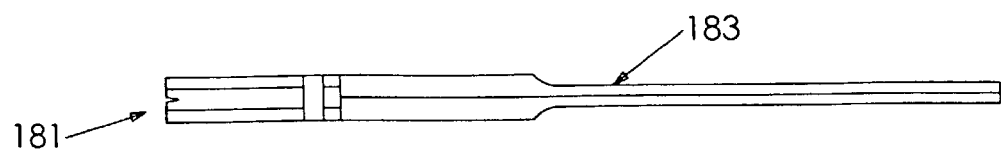
FIG. 24 is a top plan view of the applicator taken on lines 24—24 of FIG. 23.
Figure 23:
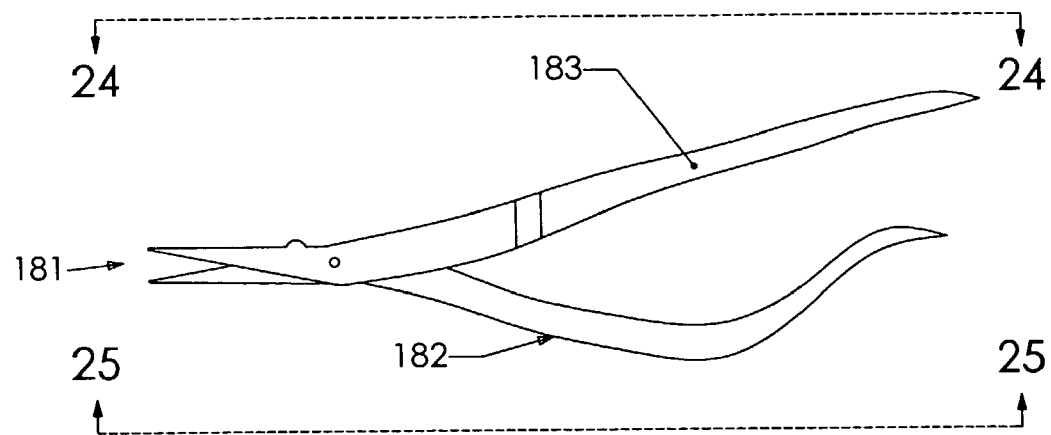
FIG. 23 is a side elevation view of the FIG. 22 applicator.
Figure 25:
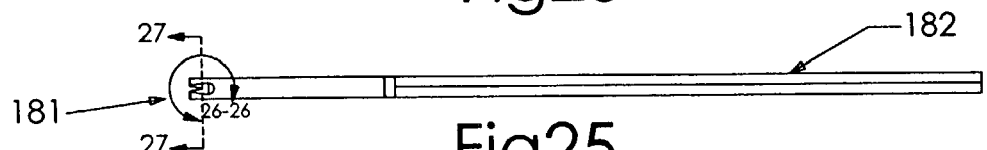
FIG. 25 is a bottom plan view taken on lines 25—25 of FIG. 23.
Figure 26:
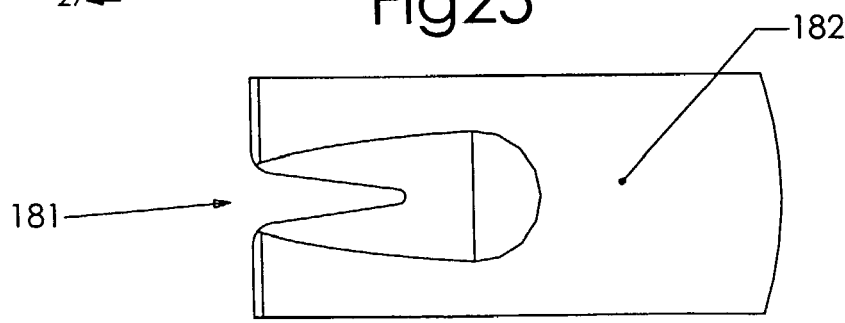
FIG. 26 is an enlarged view taken on lines 26—26 of FIG. 25.

FIGS. 20 and 21 show use of a hand manipulable applicator 110 having pusher and holder parts 60*a* and 61*a* corresponding to parts 60 and 61 referred to in FIG. 28. Hand manipulable element 111 is connected with part 61*a* via a stem 111*a*; and hand manipulable element 112 is connected with part 60*a*, so that when elements 111 and 112 are squeezed toward one another, the upper cap is relatively displaced toward the lower cap, and the caps are tightened against upper and lower surfaces of the cranial bone and bone flap. Typically, the lower cap is pulled upwardly toward and against undersides of the flap and cranial bone, during upper cap lowering. Afterwards, the post is severed, adjacent the top surfaces of the upper cap, as seen at 13*d* in FIG. 19.

Figure 32:
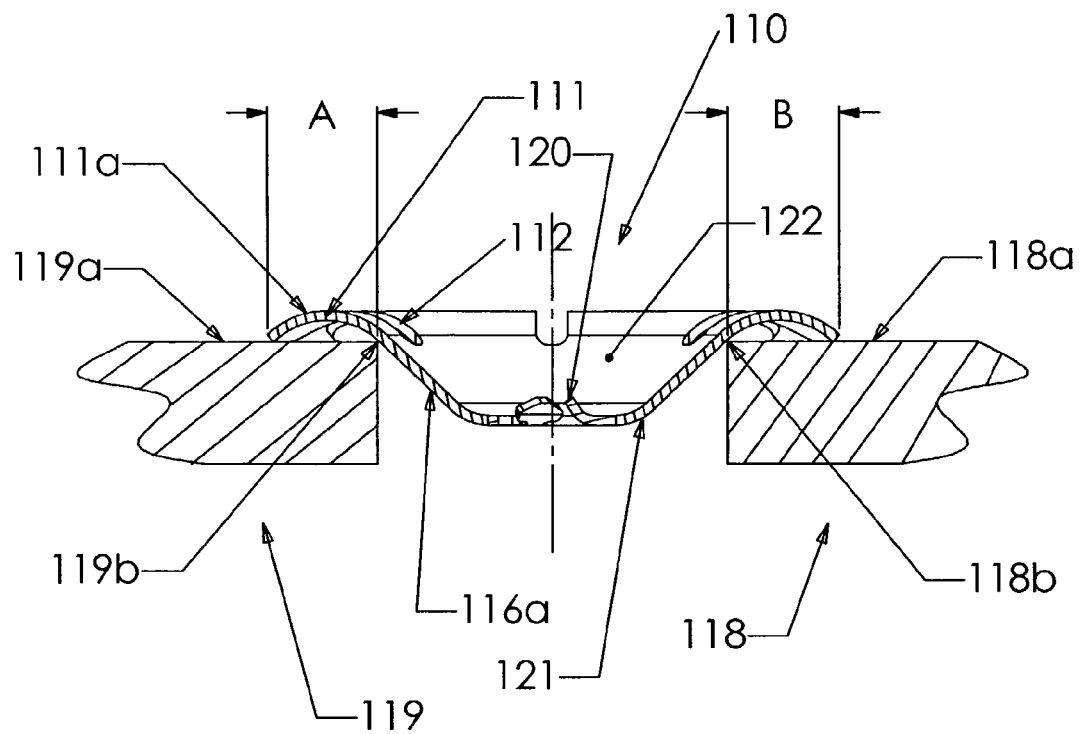
FIG. 32 is a section taken on lines 32—32 of FIG. 31.

FIGS. 29–32 show a modified form of the invention, which is preferred. The upper cap 110 has spaced petals 111 separated by slots 112 that extend inwardly toward the axis of post 113. The petals and slots are curved as seen in FIG. 32 to concavely face toward the lower cap 130. Petal edge portions 114 are turned downwardly so that edges 114*a* will grip the flap and cranial bone surfaces. Narrowed petal flexure zones are formed at 111*a*, between inner extents of the slots, allowing petal flexing to accommodate edge engagement with variably curved bone surfaces.

A protruding guide 116 is formed on, or carried on, the upper cap 110 and configured to extend or project into a gap or kerf 117 formed between cranial bone 118 and bone flap 119, at the time of installation. See FIG. 34. The cap is thereby laterally oriented so that petal portions indicated at A and B in FIG. 32 will be caused to automatically lap, to approximately equal lateral extents, the adjacent or subtended cranial bone and flap surfaces 118*a* and 119*a*, as a result of assembly. Note that the guide under surface 116*a* is generally cup-shaped, or frustoconical, to project into the gap between edges 118*b* and 119*b* of the bone surfaces at the gap upper mouth. Also note that the three post-engaging and ratcheting tabs 120, like those described in FIGS. 6–9, are carried by the bottom wall 121 of the cup-shaped guide, and a void or cavity exists at 122 above the level of those tabs.

Figure 33:
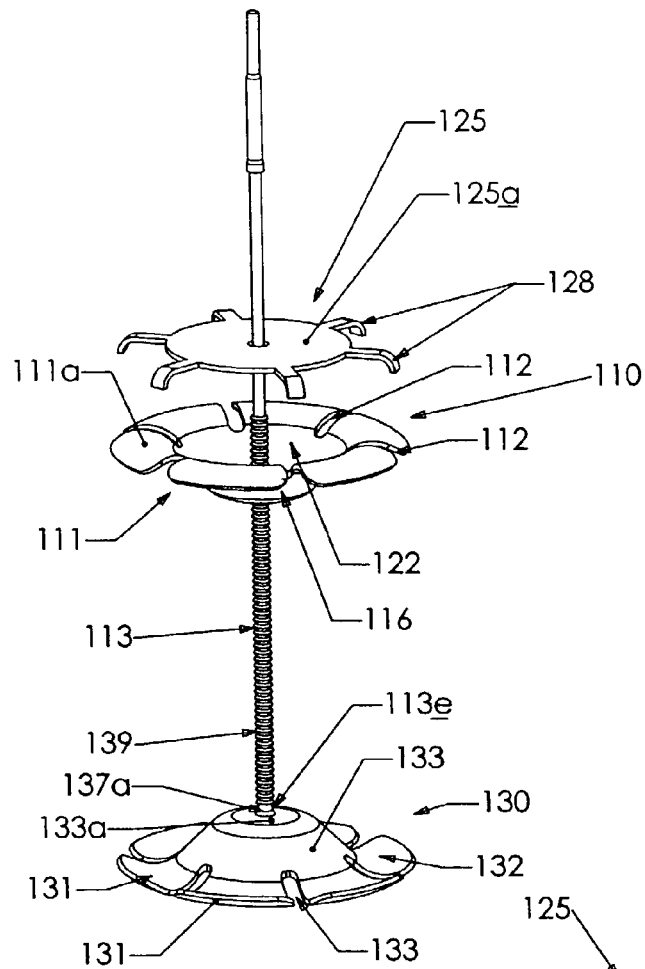
FIG. 33 is a perspective view of a further modified form of the device.
Figure 34:
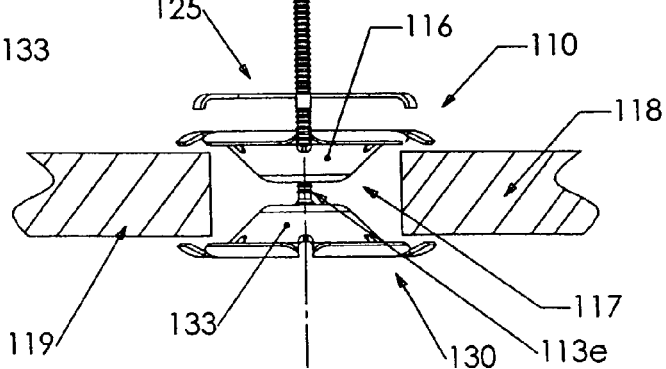
FIG. 34 is an elevation taken in section through the device of FIG. 33 during application to cranial bone and flap elements.

FIGS. 33 and 34 show the provision of a cover 125 extending over that cavity at the levels of petals, and attached to the cap. Such attachment may be effected by finger-like clips 128 projecting downwardly from the periphery of the cover plate 125a, to clip into the slots 112, plate 125a then seating on the upper surfaces 111a of petals 111. Such a cover promotes healing of scalp skin over the cap and cover, at generally the same level. The cover is typically applied after the caps are in place, gripping the bone surfaces.

The bottom cap 130 also has petals 131 like those of the upper cap, but with up-turned segment edge portions 132, those edge portions having bi-directional curvature, assuring edge gripping of bone tissue. Slots 133 are formed between petals 131, with configurations like slots 112, excepting that the petals and slots face concavely upwardly. An upwardly protruding inverted cup-shaped guide 133, like guide 116, is carried by lower cap 130 to function (with self centering) in the same manner as guide 116. See FIG. 34. The lower end 113e of post 113 is centrally attached to the end wall 133a of the guide, and it projects upwardly whereby tabs 120 can ratchet along post serrations 139, as the two caps approach one another.

Figure 35:
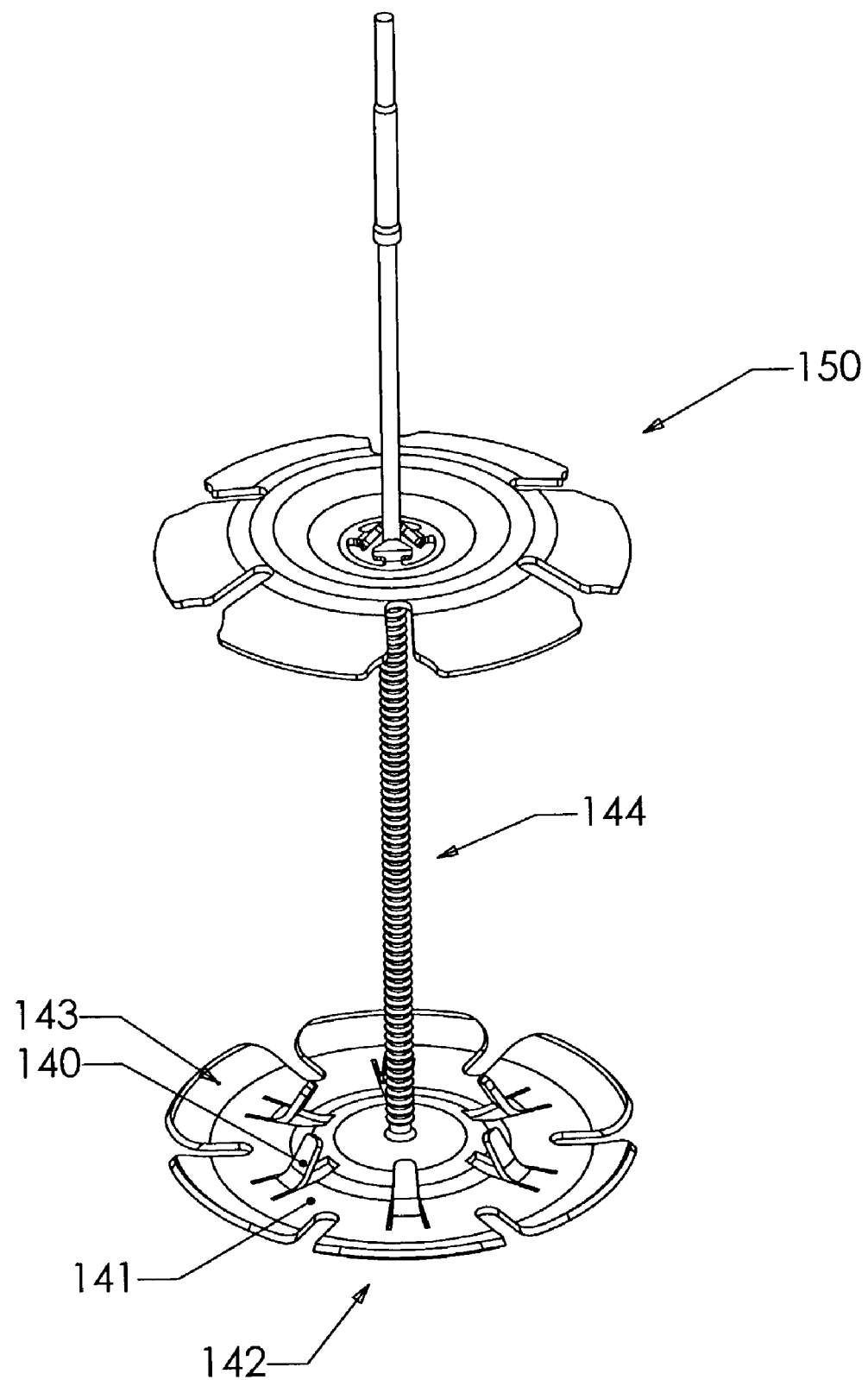
FIG. 35 is a perspective view of yet another modified form of the device.

FIG. 35 shows another embodiment of the cap orienting guide, in the form of tabs 140 projecting axially upwardly and inwardly toward the post 144 from the inner wall 141 of a lower cap 142. As shown, there is one tab spaced between each petal 143 and the post 144. The tabs provide annularly spaced and tapered surfaces engagable with the bone flap and cranial bone lower edges adjacent kerf referred to in FIG. 32, to laterally orient the lower cap, upon assembly. The upper cap 150 may have similar tabs to centrally orient it relative to the kerf or gap, upon assembly, for accurately positioning and retaining the flap, relative to the cranial bone. The provision of flexing petals allows such flexing and shifting as the caps engage bone surfaces, and as self-centering of the caps occurs due to provision of the guides.

FIGS. 22–27 show another type applicator 180, having a post gripping pincers 181, and handles 182 and 183 to cover gripping movement and release of the pincers.

We claim:

1. The method of affixing a bone flap to an adjacent cranial zone, that includes
    a) providing first and second caps between which portions of the cranial bone and bone flap are to be gripped,
    b) providing a mounting post located to allow relative cap movement lengthwise of an axis defined by the post,
    c) providing at least the first cap with peripheral petals that are spaced apart about said axis and radially outwardly of a guide defined by a central body portion of the cap, whereby the petals are individually and resiliently movable relative to said central body portion in directions generally parallel to said axis, and in response to said gripping,
    d) said guide having a thin frusto-conical side wall tapering toward and adapted to penetrate gaps of different widths between said bone flap and proximate cranial bone, said thin tapering side wall locally engaging edges of said bone flap and of said cranial bone, and there being a thin annular lower wall of the guide integral with said tapering side wall and projecting toward the post to form a central opening for passing the post, and there also being at least three tabs confined at and proximate said central opening, said tabs having narrowed flexure zones integral with said lower wall and heads spaced about the post and extending proximate the post and angled toward an interior void bounded by said tapering side wall, for interfering engagement with serrations on the post, as the cap is tightened axially along the post, said tabs everywhere confined below the upper half of said void,
    e) relatively displacing the caps toward one another whereby cap petals are engaged with at least the bone flap or the adjacent cranial bone, and to conformingly retain the caps including said petals to opposite sides of the flap and the cranial bone,
    f) tightening the caps relatively toward one another into positions wherein relative separation of the caps is blocked, petals are resiliently flexed, and post extent between the caps is tensioned, and wherein the second cap is pulled in an upward direction as the first cap is tightened downwardly.

2. The method of claim 1 including the step of causing said guide to orient the cap transversely as the cap petals approach or engage bone flap and cranial bone surfaces.

3. The method of claim 1 wherein said petals are formed as outward continuations of said guide frusto-conical wall.

4. The method of claim 1 wherein said tabs are provided to have widths less than their lengths, and define tips that have ratcheting engagement with said serrations.

5. The method of claim 1 wherein the number of said tabs is less than the number of said petals, on said one cap.

6. The method of affixing a bone flap to an adjacent cranial zone, that includes
    a) providing first and second caps between which portions of the cranial bone and bone flap are to be gripped,
    b) providing a mounting post located to allow relative cap movement lengthwise of an axis defined by the post,
    c) providing a guide on the first cap, said guide having a thin frusto-conical side wall tapering toward and adapted to penetrate gaps of different widths between said bone flap and proximate cranial bone, said thin tapering side wall locally engaging edges of said bone flap and of said cranial bone, and there being a thin annular lower wall of the guide integral with said tapering side wall and projecting toward the post to form a central opening for passing the post, and there also being at least three tabs confined at and proximate said central opening, said tabs having narrowed flexure zones integral with said lower wall and heads spaced about the post and extending proximate the post and angled toward an interior void bounded by said tapering side wall, for interfering engagement with serrations on the post, as the cap is tightened axially along the post, said tabs everywhere confined below the upper half of said void,
    d) relatively displacing the caps toward one another to first engage one cap with the underside of at least the bone flap or the adjacent cranial bone,
    e) and then tightening the caps relatively toward one another into positions wherein relative separation of the caps is blocked, and wherein the second cap pulled upwardly as the first cap is tightened relatively downwardly.

7. The method of claim 6 including causing said guide to laterally orient the first cap to have approximately equal lateral extents thereof adjacent cranial bone and bone flap surfaces.

8. The method of claim 6 wherein the second cap is pulled upwardly by pulling the post upwardly.

9. The method of claim 8 wherein the post is pulled upwardly to effect engagement of the second cap with cranial bone.

10. The method of claim 9 wherein the first cap is displaced downwardly relative to the post, and until it becomes tightened against the upper side of cranial bone.

11. The method of claim 10 wherein a hand manipulable applicator is provided and used to effect said upward pulling of the post, and said downward displacement of the first cap.

12. The method of affixing a bone flap to a cranial bone, using the following:
- a) first and second caps between which portions of the cranial bone and bone flap are to be gripped,
- b) a mounting post located to allow relative cap movement lengthwise of an axis defined by the post,
- c) at least the first cap forming peripheral petals that are spaced apart about said axis and radially outwardly of a central cup shaped guide defined by the cap, whereby the petals are individually and resiliently movable relative to said central guide in directions generally parallel to said axis, and in response to said gripping, said first cap being movable lengthwise of the post, said method including the steps:
- d) said guide having a thin frusto-conical side wall tapering toward and adapted to penetrate gaps of different widths between said bone flap and proximate cranial bone, said thin tapering side wall locally engaging edges of said bone flap and of said cranial bone, and there being a thin annular lower wall of the guide integral with said tapering side wall and projecting toward the post to form a central opening for passing the post, and there also being at least three tabs confined at and proximate said central opening, said tabs having narrowed flexure zones integral with said lower wall and heads spaced about the post and extending proximate the post and angled toward an interior void bounded by said tapering side wall, for interfering engagement with serrations on the post, as the cap is tightened axially along the post, said tabs everywhere confined below the upper half of said void,
- e) relatively displacing the caps toward one another to first engage one cap with the underside of at least the bone flap or the adjacent cranial bone,
- f) and then tightening the caps relatively toward one another into positions wherein relative separation of the caps is blocked, the second cap being pulled upwardly as the first cap is tightened downwardly.

13. The method of claim 12 wherein the first cap is displaced downwardly relative to the post, and until it becomes tightened against the upper side of cranial bone.

14. The method of claim 13 wherein a post displacing instrument is provided and used to effect said upward pulling of the post, and said downward displacement of the first cap.

15. The method of claim 14 wherein the first cap is displaced downwardly relative to the post, and until it becomes tightened against the upper side of cranial bone.

16. The method of claim 15 wherein said post displacing instrument has a gripper part used to effect said upward pulling of the post, and another part to effect said downward displacement of the first cap.

17. The method of claim 15 wherein said instrument includes two hand manipulable parts, and including the step of squeezing said parts toward one another to effect said upward pulling of the post and said downward displacement of the first cap.

* * * * *